United States Patent
Matte

(10) Patent No.: US 9,446,295 B2
(45) Date of Patent: Sep. 20, 2016

(54) TETHERED TRAINING HARNESS

(71) Applicant: Sylvain Matte, Burlington, CA (US)

(72) Inventor: Sylvain Matte, Burlington, CA (US)

(73) Assignee: SYLVAIN MATTE, Burlington (CA)

( * ) Notice: Subject to any disclaimer, the term of this patent is extended or adjusted under 35 U.S.C. 154(b) by 0 days.

(21) Appl. No.: 14/785,722

(22) PCT Filed: Apr. 22, 2013

(86) PCT No.: PCT/CA2013/050309
§ 371 (c)(1),
(2) Date: Oct. 20, 2015

(87) PCT Pub. No.: WO2014/172771
PCT Pub. Date: Oct. 30, 2014

(65) Prior Publication Data
US 2016/0067578 A1    Mar. 10, 2016

(51) Int. Cl.
| | |
|---|---|
| A63B 69/18 | (2006.01) |
| A63B 69/00 | (2006.01) |
| A47D 13/08 | (2006.01) |
| A62B 35/00 | (2006.01) |
| A61F 5/37 | (2006.01) |
| A63B 69/12 | (2006.01) |
| A63B 69/16 | (2006.01) |
| A63B 21/04 | (2006.01) |

(Continued)

(52) U.S. Cl.
CPC ......... *A63B 69/0048* (2013.01); *A47D 13/086* (2013.01); *A61F 5/37* (2013.01); *A62B 35/00* (2013.01); *A63B 69/12* (2013.01); *A63B 69/16* (2013.01); *A63B 69/18* (2013.01); *A63B 21/0442* (2013.01); *A63B 21/0552* (2013.01); *A63B 21/153* (2013.01); *A63B 21/28* (2013.01); *A63B 21/4005* (2015.10); *A63B 23/047* (2013.01); *A63B 2208/12* (2013.01); *A63C 2201/12* (2013.01)

(58) Field of Classification Search
USPC ........... 434/247, 253, 255; 119/770; 482/51, 482/66, 69, 92, 95, 121
See application file for complete search history.

(56) References Cited

U.S. PATENT DOCUMENTS

| | | | |
|---|---|---|---|
| 3,088,438 A * | 5/1963 | Oliphant | A01K 27/004 119/770 |
| 4,308,629 A | 1/1982 | Freemon | |

(Continued)

FOREIGN PATENT DOCUMENTS

| | | |
|---|---|---|
| DE | 3521146 A1 | 12/1986 |
| EP | 0561125 B1 | 10/1996 |
| WO | 00/54842 | 9/2000 |

OTHER PUBLICATIONS

International Search Report and Written Opinion for PCT/CA2013/050309 dated Oct. 22, 2013.

*Primary Examiner* — Kurt Fernstrom
(74) *Attorney, Agent, or Firm* — Knobbe, Martens, Olson & Bear LLP

(57) ABSTRACT

Described herein is a training harness comprising: a harness comprising at least one anchor point connecter; and a retractable tether comprising a casing supporting and storing a rotatable spool, a handle grip connected to the casing, a tether comprising a first end coupled to the spool and a second end configured for reversible coupling to the at least one anchor point connecter, an elastic section at or proximal to the second end. The training harness may be used by children learning a sport, particularly a downhill gliding sport such as skiing or snowboarding.

23 Claims, 4 Drawing Sheets

(51) Int. Cl.
*A63B 21/055* (2006.01)
*A63B 21/00* (2006.01)
*A63B 21/28* (2006.01)
*A63B 23/04* (2006.01)

(56) References Cited

U.S. PATENT DOCUMENTS

| | | | |
|---|---|---|---|
| 4,424,040 A | 1/1984 | Buchheister et al. | |
| 4,445,866 A | 5/1984 | Cillieres | |
| 4,505,681 A * | 3/1985 | Jones | A63C 11/10 |
| | | | 273/DIG. 19 |
| 4,509,921 A * | 4/1985 | Buchheister | A63B 69/18 |
| | | | 434/253 |
| 4,666,017 A | 5/1987 | Zimmerman | |
| 4,667,624 A * | 5/1987 | Smith | A01K 27/00 |
| | | | 119/770 |
| 5,074,795 A * | 12/1991 | Clark | A47D 13/086 |
| | | | 119/770 |
| 5,388,551 A * | 2/1995 | Martusciello | A01K 27/002 |
| | | | 119/770 |
| 5,638,772 A * | 6/1997 | Kaufmann | A01K 27/005 |
| | | | 119/770 |
| 5,842,444 A * | 12/1998 | Perrulli | A01K 27/003 |
| | | | 119/770 |
| 6,651,594 B1 * | 11/2003 | Bagwell | A47D 13/086 |
| | | | 119/770 |
| 6,851,393 B2 * | 2/2005 | Bremm | A01K 27/003 |
| | | | 119/770 |
| 7,384,382 B2 * | 6/2008 | Farrah | A63B 21/153 |
| | | | 273/453 |
| 7,516,717 B2 * | 4/2009 | David | A01K 27/00 |
| | | | 119/770 |
| 7,866,282 B2 * | 1/2011 | Simpson | A01K 1/04 |
| | | | 119/781 |
| 7,900,586 B2 * | 3/2011 | Hamblen | A47D 13/086 |
| | | | 119/770 |
| 8,336,503 B2 * | 12/2012 | Spinelli | A47D 13/086 |
| | | | 119/770 |
| 2003/0057018 A1 | 3/2003 | Dodson | |
| 2004/0018922 A1 * | 1/2004 | Maiuri | A63B 21/0552 |
| | | | 482/124 |
| 2015/0031007 A1 | 1/2015 | Ruiz | |
| 2015/0099251 A1 | 4/2015 | Anderson | |

* cited by examiner

TETHERED TRAINING HARNESS

CROSS REFERENCE TO RELATED APPLICATIONS

This application is the U.S. National Phase of International Application No. PCT/CA2013/050309, filed Apr. 22, 2013, designating the U.S. and published in English as WO 2014/172771 on Oct. 30, 2014. Any and all applications for which a foreign or domestic priority claim is identified here or in the Application Data Sheet as filed with the present application are hereby incorporated by reference under 37 CFR 1.57.

BACKGROUND OF THE INVENTION

1. Field of the Invention

The present invention relates to a training harness, and more particularly a training harness for learning a sport.

2. Description of the Related Art

A child learning a body balanced motor activity, such as walking, swimming, bicycling, skiing, snowboarding, skating, and the like, typically requires many repetitions and failures prior to achieving consistent competency and confidence in performing the activity. Wearing a training harness with reins or tethers that allow a supervisor to guide and assist the child's body posture or motion can expedite the learning process.

Several training harnesses have been described. For example U.S. Pat. No. 4,308,629 (issued 5 Jan. 1982), U.S. Pat. No. 4,424,040 (issued 3 Jan. 1984), U.S. Pat. No. 4,505,681 (issued 19 Mar. 1985), U.S. Pat. No. 4,666,017 (issued 19 May 1987), U.S. Pat. No. 4,667,624 (issued 26 May 1987), U.S. Pat. No. 5,074,795 (issued 24 Dec. 1991), and European Patent Publication No. 0561125 (published 22 Sep. 1993) all describe functional harnesses that allow a child to experience ranges of movement under control of a supervisor holding a rein or tether. However, in each of these disclosures the rein or tether is awkward and bulky to store and may be a hazard in becoming entangled with the child's limbs or on a structure in the child's immediate environment. For example, for a child learning to ski or snowboard entanglement of the rein or tether is a particular danger when getting on or off of a chair lift.

Accordingly, there is a continuing need for alternative tethered training harnesses.

SUMMARY OF THE INVENTION

In an aspect there is provided a training harness comprising:

a harness comprising a back panel, a pair of shoulder straps connected to the pack panel, a waist strap connected to the back panel, and at least one sliding anchor point connecter; and a retractable tether comprising a casing supporting and storing a rotatable spool, a handle grip connected to the casing, a tether comprising a first end coupled to the spool and a second end configured for reversible coupling to the at least one sliding anchor point connecter, an elastic section at or proximal to the second end.

In another aspect there is provided a training harness comprising:

a back panel, a pair of shoulder straps connected to the pack panel, a waist strap connected to the back panel, at least one runner mounted on the back panel, and an elastic tether comprising a first end coupled to the runner and a second end configured for reversible coupling to a retractable tether.

In yet another aspect there is provided a retractable tether comprising:

a casing supporting and storing a rotatable spool and a tether, the tether comprising a first end coupled to the spool and a second end configured for reversible coupling to a training harness, an elastic section at or proximal to the second end, a handle grip connected to the casing, a hook connected to the casing, the hook configured for reversibly engaging a closed loop of the training harness.

In still another aspect there is provided a training harness comprising:

a harness comprising at least one anchor point connecter; and a retractable tether comprising a casing supporting and storing a rotatable spool, a handle grip connected to the casing, a tether comprising a first end coupled to the spool and a second end configured for reversible coupling to the at least one anchor point connecter, an elastic section at or proximal to the second end.

DETAILED DESCRIPTION OF THE PREFERRED EMBODIMENT

Figure 1:
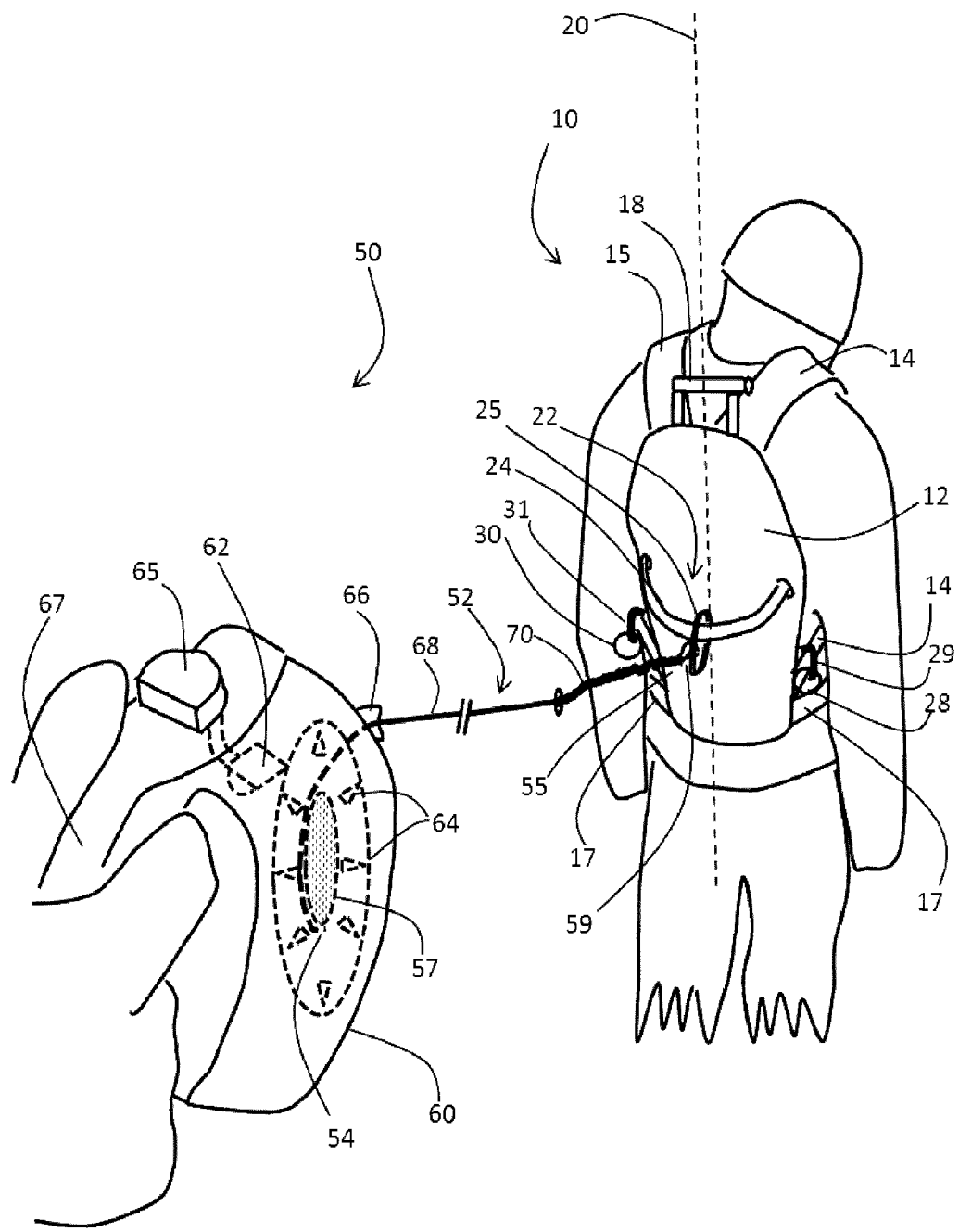
FIG. 1 shows a back perspective view of a training harness with a retractable tether.

Referring to the drawings, FIG. 1 shows a training harness 10 with a retractable tether 50.

The training harness comprises a back panel 12, a pair of shoulder straps 14, 15, and a waist strap 17. The pair of shoulder straps 14, 15 and the waist strap 17 are connected to the back panel 12. A handle 18 is connected at a top portion of the back panel 12.

The back panel 12 has a generally elongate shape defining a longitudinal direction and a transverse lateral direction. The back panel 12 and shoulder straps define a longitudinal line of symmetry 20. The handle 18 is oriented transverse to the line of symmetry 20.

A runner 22 providing a slidable connection point for retractable tether 50 is also oriented transverse to the line of symmetry 20. Runner 22 comprises an arcuate rod 24 and a closed ring 25 that slides along the length of the arcuate rod 24. The closed ring 25 provides a slidable anchor point connecter for the retractable tether 50. The arcuate rod 24 comprises two opposing ends connected to the back panel 12 at substantially equidistant points from the line of symmetry 20. The two opposing ends connected to the back panel are approximately 15 cm apart. The curvature of the arcuate rod is approximately 30 degrees and the curved length of the arcuate rod is approximately 25 cm.

Two further anchor point connectors for the retractable tether 50 are provided by closed rings 28, 30 that are slidably coupled to shoulder straps 14 and 15, respectively. Closed ring 28 is coupled to shoulder strap 14 by connecting strap 29, while closed ring 30 is coupled to shoulder strap 15 by connecting strap 31.

Retractable tether 50 may be coupled to one or more of the closed rings 25, 28, 30. Any conventional retraction mechanism may be used to control retraction and/or extension of the retractable tether. The retractable tether 50 comprises a flexible tether 52 having a first end 54 and a second end 55, the first end connected to a rotating spool 57 and the second end pivotally coupled to a quick-release snap hook connecter 59 for attachment to at least one of closed rings 25, 28, 30. The rotational spool and cord is stored in a casing 60. The spool is rotatably supported within the casing for carrying the flexible tether, the flexible tether being wound around the spool and extending externally of from the casing for the unwinding of the flexible tether. A brake 62 located within the casing can engage a plurality of evenly spaced surfaces, such as teeth 64, to stop rotation of the spool. An actuator 65 extends from the casing, the actuator operationally coupled to the brake 62. The actuator has a first default position which does not activate the brake, and a second position that activates the brake. the A biasing mechanism (not shown) such as a coiled leaf spring may be connected to the spool to bias retraction of the flexible tether. The casing 60 defines an opening 66 for communication of the flexible tether into and out of the casing. A handle grip 67 is integrally molded with the casing proximal to actuator 65 to allow for hand held operation of the retractable tether and single handed actuation of the brake 62.

The flexible tether 52 comprises sections of differing elasticity. The flexible tether comprises a non-elastic section 68 at the first end 54 of the flexible tether 52, and an elastic section 70 at or proximal to the second end 55 of the flexible tether 52. More specifically, a first end of the non-elastic section 68 is connected to the spool 57, a second end of the non-elastic section is coupled to a first end of the elastic section 70, and a second end of the elastic section is permanently attached to quick-release snap hook connecter 59.

Consistent with nomenclature, the elasticity of the elastic section 70 is greater than the non-elastic section 68 of the flexible tether 52. The elastic section 70 has a first resting length and a second tensioned elastic length. The maximal second tensioned elastic length of the elastic section 70 is generally at least 20% greater than the first resting length. More specifically in the example shown in FIG. 1, the maximal second tensioned elastic length (45 cm) is approximately 50% greater than the first resting length (30 cm).

Figure 2:
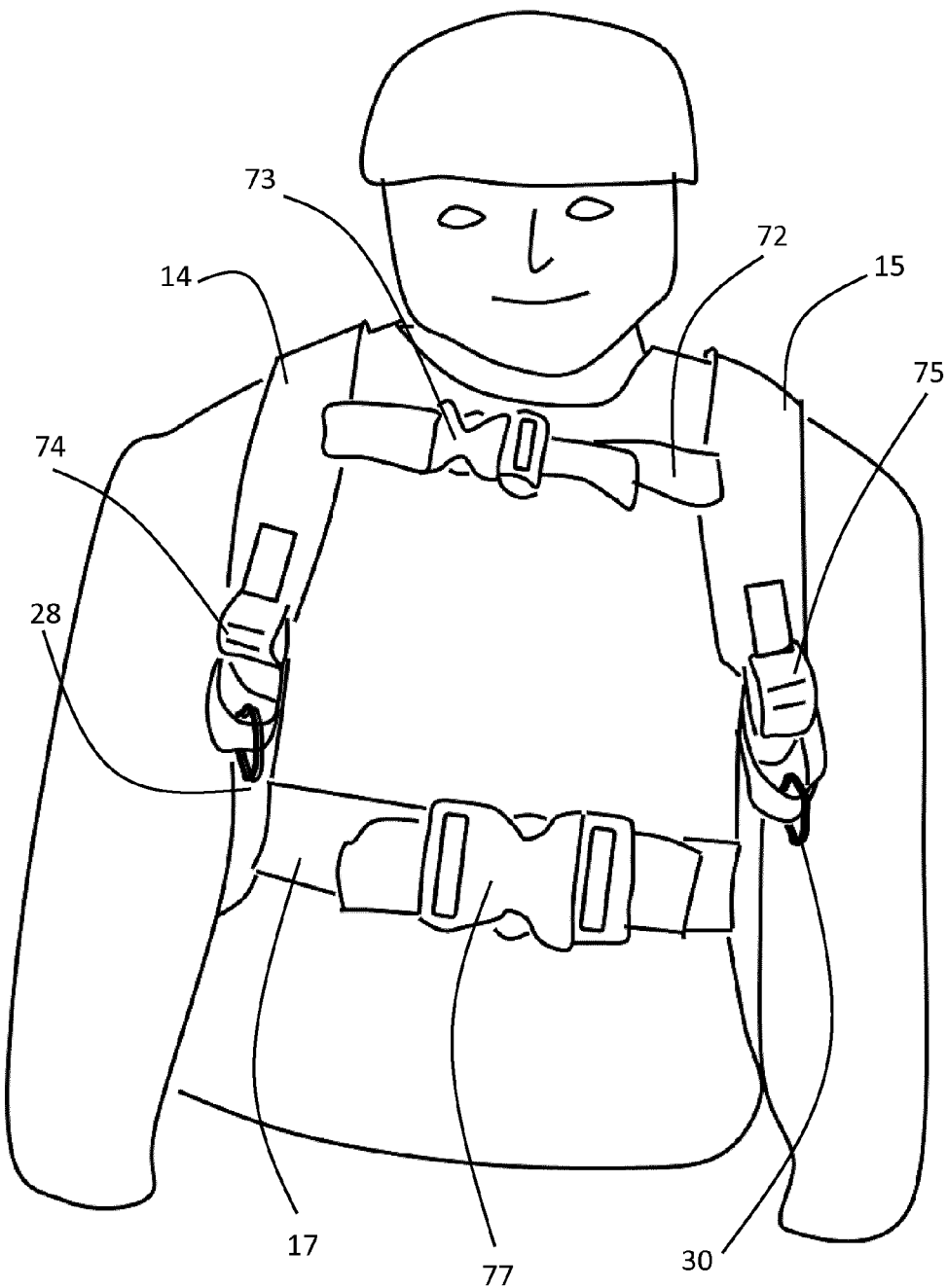
FIG. 2 shows a front perspective view of the training harness shown in FIG. 1.

FIG. 2 shows a front view of the harness 10. Shoulder straps 14 and 15 comprise adjustable buckles 74 and 75, respectively. Cross-strap 72 enhances fitting of the harness on a trainee by linking shoulder straps 14 and 15. Cross-strap 72 comprises a side quick-release connecter 73. The side quick-release connecter comprises two halves: a male half comprised of two prongs with hooked ends, and; a female half comprising a bucket defining a cavity for receiving the prongs, the sides of the bucket defining openings for engaging the hooked ends. The male half of quick-release connector 73 comprises a buckle for adjusting the length of the cross-strap 72. Waist strap 17 comprises a side quick-release connecter 77. The side quick-release connecter comprises two halves: a male half comprised of two prongs with hooked ends, and; a female half comprising a bucket defining a cavity for receiving the prongs, the sides of the bucket defining openings for engaging the hooked ends. Both the male and female halves of quick-release connector 77 comprises buckles for adjustably engaging portions of the waist strap 17.

Figure 3:
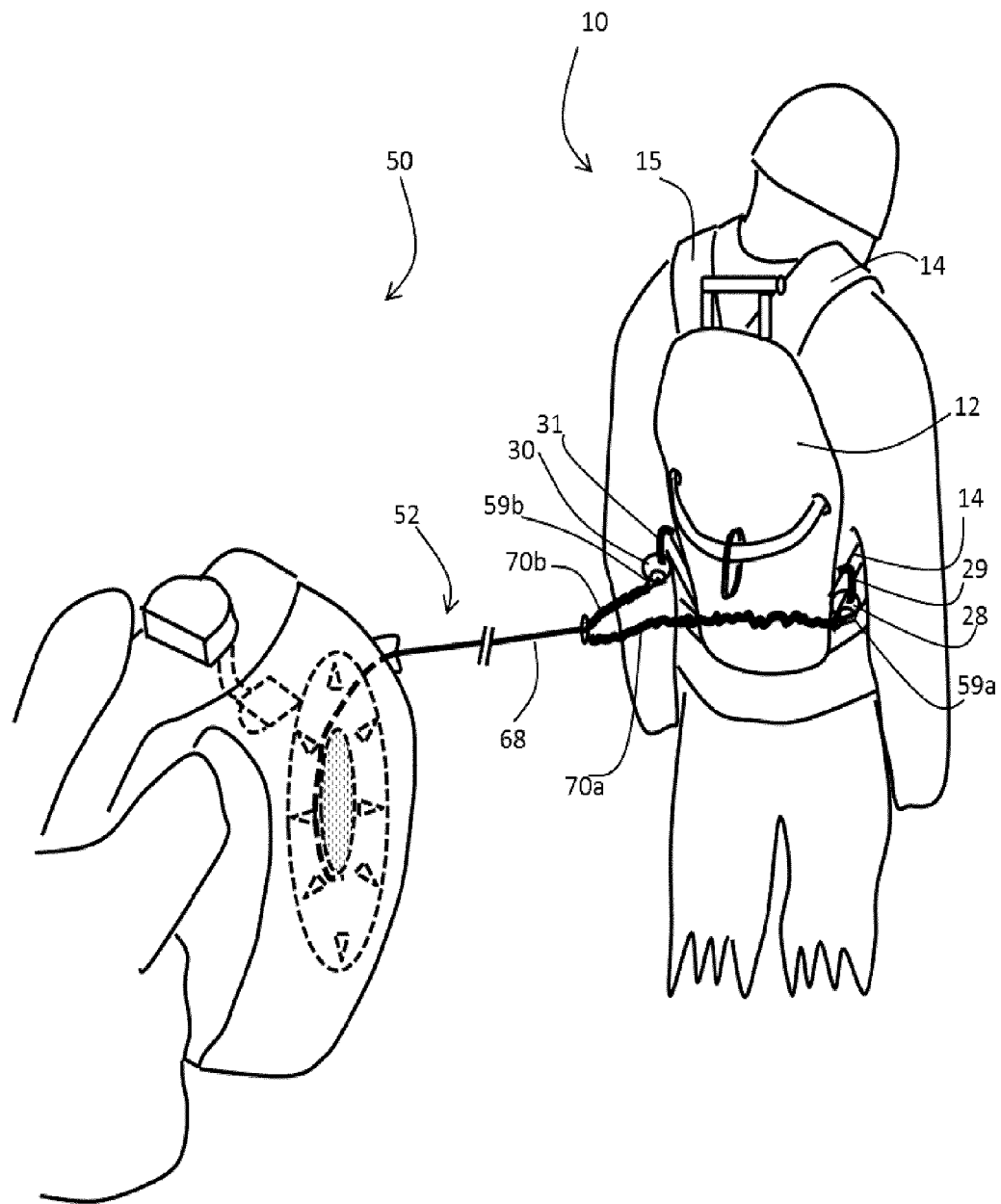
FIG. 3 shows a back perspective view of the training harness shown in FIG. 1 with an alternative retractable tether.

FIG. 3 shows the training harness shown in FIG. 1 with the retractable tether comprising an alternate configuration of the elastic section 70. The elastic section is comprised of two arms 70a, 70b of substantially the same length and elasticity. The two elastic section arms 70a and 70b each have a first end coupled to the second end of the non-elastic section 68, and a second end permanently attached to quick-release snap hook connecters 59a and 59b, respectively which in turn are coupled to closed rings 28 and 30, respectively.

Figure 4:
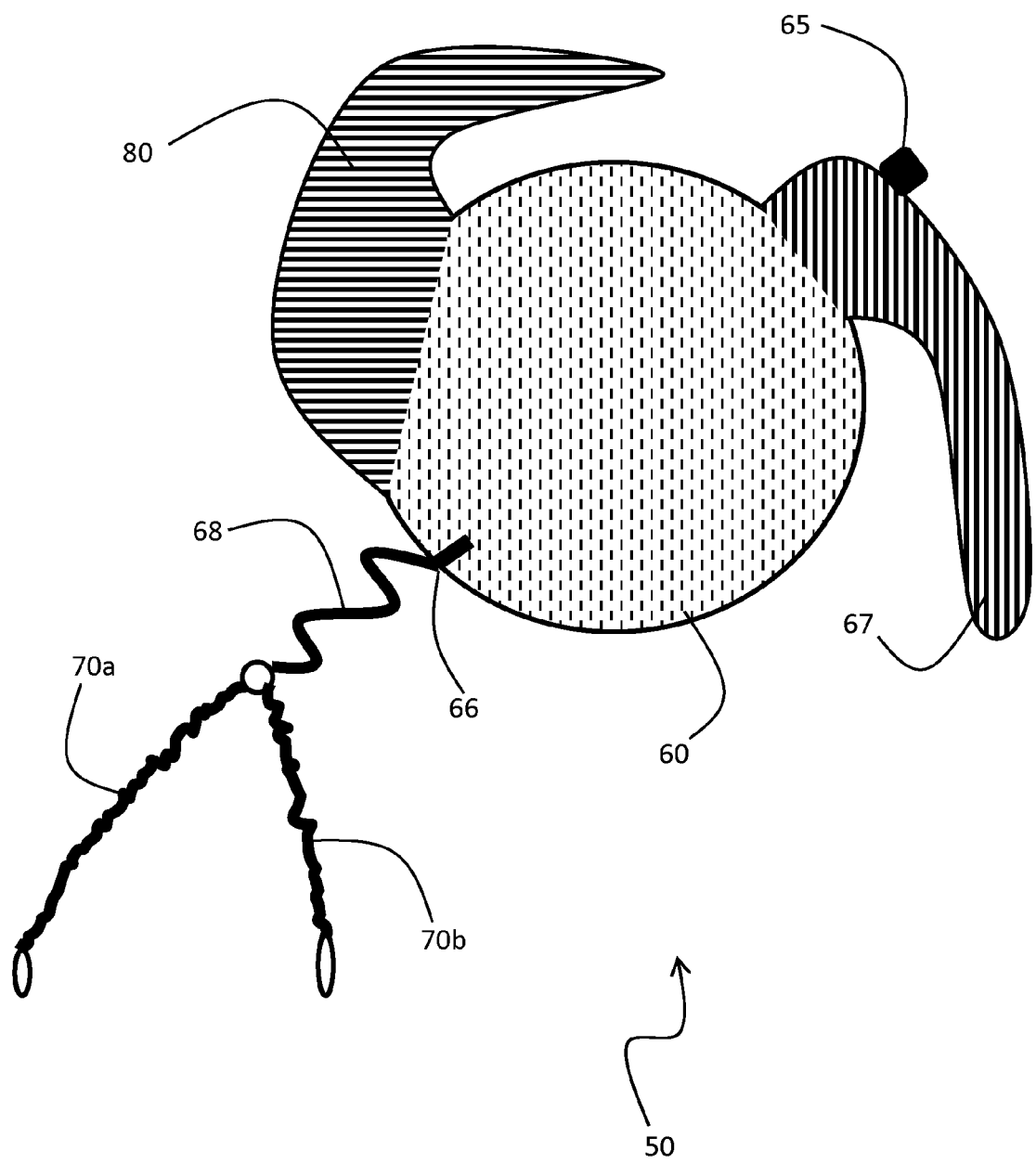
FIG. 4 shows a plan view of another alternative retractable tether decoupled from the training harness.

FIG. 4 shows a retractable tether 50 comprising an alternative casing. Hook 80 is integrally molded with casing 60. Hook 80 may be used to engage arcuate rod 24 or handle 18 to lift or control a user wearing the harness 10.

In use, the harness 10 may be worn by the trainee throughout both active and rest periods during a training session. The retractable tether 50 may be coupled to the harness and extended during active periods, and retracted during rest periods. As long as retraction occurs, decoupling of the tether from the harness 10 may not be needed during a rest period. For example, without decoupling a casing storing a retracted tether could be placed in a holding compartment formed in the back panel 12. The back panel 12 may comprise any number of conventional holding compartments such as pockets, pouches, back packs and the like. The holding compartment is typically formed of two opposing surfaces joined along a circumference of at least one of the surfaces defining an interior cavity and a sealable opening communicating with the interior cavity, the sealable opening fitted with a reversible fastener, such as pile-type Velcro, magnets, snap buttons, zippers and the like. Alternatively, a clip may be mounted on a surface of the casing and during rest periods the casing storing a retracted tether can be coupled by the clip to a shoulder or waist strap of the harness, again without need for decoupling of the tether from the harness.

The retractable tether provides a quick mechanism to remove a potential hazard of entanglement of the tether with the limbs of the trainee during rest periods. Some examples of danger posed by entanglement of a tether in limbs or surrounding structures are a skier or snowboarder trainee getting on or off of a chair lift, or a swimmer trainee climbing out of a pool.

The harness 10 and retractable tether 50 combination also provide advantages during active periods. The retractable tether allows a supervisor/trainer to adjust the distance from the trainee as desired up to a maximum defined by the length of the tether. The elastic section of the tether cushions the trainee from a jarring action that occurs when a brake is applied while the tether is being unwound or as the tether reaches its unwound limit.

Slidable coupling of the tether to the harness such as provided by runner 22 allows the trainee a greater range of motion, while maintaining control by the supervisor/trainer. A slidable coupling may also reduce a jarring action that may occur when a trainee and/or trainer alter their physical orientation while in motion.

A hook connected to the casing may provide several training benefits. A hook can engage a component of a harness, such as a handle or a runner, to lift a trainee that has fallen, to lift a trainee into a chair lift, or even for initial guidance during a training run. For example, with a retractable tether in a wound position coupled to an anchor point connecter a trainer may engage a component of the harness with the hook to stay in motion in physical contact with the trainee. The trainer can then decide to disengage the hook and allow the retractable tether to unwind while remaining in motion.

Several variants of a training harness with a retractable tether have been described above. Still further examples of variants now follow.

The training harness may be used for training in a number of different sports or body balanced motor activity, such as walking, swimming, bicycling, skiing, snowboarding. The training harness may be particularly useful for downhill gliding sports such as skiing and snowboarding.

Any conventional mechanism of retraction may be used for the retractable tether. Typically such mechanisms will comprise a casing supporting a rotating spool and a tether having one end connected to the spool. One or more of the many different conventional mechanisms for controlling rotation of the spool may be used including, for example, a crank arm actuator for winding and unwinding the tether, spring biased rotation of the spool to wind the tether, a brake to stop rotation of the spool, a lock to maintain the brake on the spool, etc.

Any form of tether may be used including cables, cords, ropes, wires, straps and the like, provided that the tether may be wound and unwound from a rotatable spool supported in a casing. The tether may be made of any convenient material or any combination of material such as nylon or leather. The tether may be of any desired length, typically ranging between 100 cm and 1000 cm.

The elastic section need not be at the end of the tether used for coupling the harness. For example, in a version where the tether terminates with a plurality of arms coupling to a plurality of anchor point connecters on the harness, such as shown in FIG. 3, the plurality of arms may be non-elastic and coupled to a single armed elastic section which in turn is serially coupled to a non-elastic section that connects to the spool. Thus, the elastic section will typically be at or proximal to the end of the tether that couples to the harness.

The material used for the elastic section may comprise any elastic material such as rubber. Any combination of materials may be used provided that the elastic section has a first resting length and a second tensioned elastic length, the maximal second tensioned elastic length generally being at least 20% greater than the first resting length. For example, with a 20% increase a first resting length of 10 cm allows for a maximal second tensioned elastic length of 12 cm. Typically, the maximal second tensioned will be greater than the first resting length by at least 20%, 25%, 30%, 35%, 40%, 45%, 50%, 55% or any percentage therebetween.

The first resting length of the elastic section will be at least 3 cm, typically ranging between 6 cm and 60 cm.

The elastic section may be omitted provided that the trainee wearing the training harness is willing to accept jarring caused by applying a brake to the retractable tether or by the tether fully unwinding from the spool.

The non-elastic section may have some elasticity and need not be unyielding to tensioned stretching and reversion to original form upon release from tension. The non-elastic section may possess elastic properties, such as the commercially available Paracord known for its semi-elastic properties. Qualitatively, the non-elastic section will be less elastic that the elastic section. Quantitatively, elasticity may be characterized by Young's Modulus values, often expressed as GigaPascals (1 GigaPascal converts to $10^9$ N/m$^2$) with lower values indicating greater elasticity. The Young's Modulus value of the non-elastic section will generally be at least 3 times (ie. 300%) greater than the Young's Modulus of the elastic section. Typically, the Young's Modulus value of the non-elastic section will be greater than the Young's Modulus of the elastic section by at least 300%, 400%, 500%, 600%, 700%, 800%, 900%, 1000% or any percentage therebetween.

The elastic and non-elastic sections may be coupled using any conventional method including both permanent and reversible couplings, for example, clamps, clips, stitching, quick-release connecters and the like.

Similarly, the tether and the harness may be coupled using any conventional method including both permanent and reversible couplings, for example, clamps, clips, stitching, quick-release connecters and the like. However, reversible couplings such as quick-release connecters provide greater convenience and flexibility and are likely to be used more frequently than permanent couplings. A snap hook (sometimes referred to as a snap clip) is an example of a quick-release connecter. Snap hooks generally comprise a hooked portion and a clasp moveable by manual force between an open position and a closed position, the clasp biased to the closed position.

Many different harness structures may be used in combination with the retractable tether. Typically, the harness will comprise a waist strap. Where a back panel is absent, the shoulder straps may be connected to the waist strap. Additional straps may be used as desired. For example, FIG. 2 shows an adjustable cross-strap linking the front portion of the pair of shoulder straps.

A back panel is not necessary, but is useful to provide a secure fit for the harness, a surface for attachment of anchor point connecter for coupling to the tether, and/or a surface for a holding compartment such as a pocket, backpack or pouch.

A harness may comprise a waist strap without shoulder straps. In this version the waist strap will typically have a greater width than waist straps used in combination with shoulder straps and the back panel. A harness comprising a waist strap without shoulder straps will generally be at least 5 cm wide, typically ranging from 5 cm to 20 cm.

The runner 22 may take any form as long as a sliding mechanism is provided. For example, a rod and ring structure may be used as shown in FIGS. 1 and 3. The rod may be curved or straight. A stiff strap or lanyard may be used instead of the rod. For example, the shoulder sliding anchor point shown in FIGS. 1 and 3 is a runner in the form of a ring strap engaging a linear strap. As another example, a sliding track may be used as a runner. Typically, an outer track mounted on the harness is coupled to a shorter inner track or bolt with ball bearings disposed between the walls of the inner track or bolt and the outer track and the tether coupled to the inner track or bolt. The runner may comprise a detent mechanism. For example, with both the rod and ring structure and the sliding track structure, notches may be used to provide for detent. Detent mechanisms may be provided at one or more positions along the runner, for example, at center, left of center, and/or right of center.

A plurality of runners may be mounted on the harness or a single runner may be used. The length of the runner can be set as desired, but will typically range between 10 cm and 50 cm. The runner may be straight or curved as desired, typically ranging from no curve to a curve of 180 degrees.

Anchor point connecters may be stationary provided that the trainee and trainer are will to accept a limited range of motion in comparison to use of sliding anchor point connecters.

The casing of the retractable tether may take a variety of forms known for retractable mechanisms. The retractable tether may optionally comprise a handle grip connected to the casing. Various handle grips are contemplated including a handle grip mounted to a peripheral surface of the casing or a handle grip integrally molded with the casing. The retractable tether may also optionally comprise a hook connected to the casing. Various hooks are contemplated including mounting a hook on a peripheral surface of the casing or integrally molding the hook with the casing. The retractable tether may also optionally comprise a belt clip connected to the casing. Various clips are contemplated including a clip mounted to a side surface of the casing or a handle grip integrally molded with the casing. A belt clip may provide several benefits including, for example, hands-free operation of the tether by clipping the casing to the waist of a supervisor/trainer during an active period, or clipping the casing to the waist of the trainer or the trainee during a rest period.

A hook connected to a casing may provide several benefits. A hook can engage a component of a harness, such as a handle or a runner, to lift a trainee that has fallen, to lift a trainee into a chair lift, or even for initial guidance during a training run. Using the hook prevents strain on the back of the supervisor/trainer. The arm of the hook spaced from the casing surface will generally be at least 4 cm long from the point that it approaches the casing surface to its free end, the length typically ranging from 5 cm to 20 cm depending on casing dimensions. Spacing between the free end of the hook and the casing surface will generally be at least 2 cm, typically ranging from 2 cm to 9 cm depending on dimensions/diameter of a targeted harness component, such as a runner or handle.

Still further variants, equivalents, and combinations thereof will be apparent to the person of skill in the art on a full reading of the specification and drawings.

What is claimed is:

1. A training harness for a downhill gliding sport comprising:
   a harness comprising a back panel, a pair of shoulder straps connected to the back panel, a waist strap connected to the back panel, and at least one sliding anchor point connecter; and
   a retractable tether comprising a casing supporting and storing a rotatable spool, a handle grip connected to the casing, a tether comprising a first end coupled to the spool and a second end configured for reversible coupling to the at least one sliding anchor point connecter, an elastic section at or proximal to the second end, and a hook connected to a circumferential surface of the casing, the hook configured for reversibly engaging the harness.

2. The training harness of claim 1, wherein the at least one sliding anchor point connecter is a runner comprising a rod connected at first and second ends to the back panel and a closed ring slidably engaging the rod.

3. The training harness of claim 2, wherein the back panel and shoulder straps define a longitudinal line of symmetry and the runner is oriented transverse to the line of symmetry.

4. The training harness of claim 1, wherein the hook is mounted on the casing.

5. The training harness of claim 1, wherein the hook is integrally molded with the casing.

6. The training harness of claim 1, further comprising a clip connected to a side surface of the casing.

7. The training harness of claim 1, wherein the back panel is a back pack comprising first and second surfaces circumferentially connected to define an interior cavity and a sealable opening communicating with the interior cavity.

8. The training harness of claim 1, further comprising a brake enclosed within the casing, the brake operationally associated with a plurality of surfaces of the spool, and the brake configured to engage one of the plurality of surfaces of the spool to prevent rotation of the spool.

9. The training harness of claim 1, wherein the spool is biased to rotate in a direction to retract the tether.

10. The training harness of claim 2, wherein the second end comprises a quick-release connecter for engaging the closed ring.

11. The training harness of claim 1, wherein the elastic section is at the second end.

12. The training harness of claim 1, wherein the downhill gliding sport is snowboarding.

13. A training harness for a downhill gliding sport comprising:
    a harness comprising a back panel, a pair of shoulder straps connected to the back panel, a waist strap connected to the back panel, and a pair of anchor point connecters symmetrically coupled to the harness; and
    a retractable tether comprising a casing supporting and storing a rotatable spool, a handle grip connected to the casing, a tether comprising a first end coupled to the spool and a second end comprising a pair of elastic section arms, each of the pair of elastic section arms configured for reversible coupling to one of the pair of anchor point connectors, and a hook connected to a circumferential surface of the casing, the hook configured for reversibly engaging the harness.

14. The training harness of claim 13, further comprising a handle connected to the back panel, the handle configured for reversibly engaging the hook.

15. The training harness of claim 14, wherein the back panel and shoulder straps define a longitudinal line of symmetry and the handle is oriented transverse to the line of symmetry.

16. The training harness of claim 13, wherein the hook is mounted on the casing.

17. The training harness of claim 13, wherein the hook is integrally molded with the casing.

18. The training harness of claim 13, further comprising a clip connected to a side surface of the casing.

19. The training harness of claim 13, wherein the back panel is a back pack comprising first and second surfaces circumferentially connected to define an interior cavity and a sealable opening communicating with the interior cavity.

20. The training harness of claim 13, further comprising a brake enclosed within the casing, the brake operationally associated with a plurality of surfaces of the spool, and the brake configured to engage one of the plurality of surfaces of the spool to prevent rotation of the spool.

21. The training harness of claim 13, wherein the spool is biased to rotate in a direction to retract the tether.

22. The training harness of claim 13, wherein each of the pair of elastic section arms comprises a quick-release connecter configured for reversible coupling to one of the pair of anchor point connectors.

23. The training harness of claim 13, wherein the downhill gliding sport is snowboarding.

* * * * *

UNITED STATES PATENT AND TRADEMARK OFFICE
CERTIFICATE OF CORRECTION

PATENT NO. : 9,446,295 B2  Page 1 of 1
APPLICATION NO. : 14/785722
DATED : September 20, 2016
INVENTOR(S) : Sylvain Matte It is certified that error appears in the above-identified patent and that said Letters Patent is hereby corrected as shown below:

At item (71) on the title page of the patent, please replace the Applicant's address "Burlington, CA (US)" with --Oro-Medonte, Ontario, CA--.

At item (72) on the title page of the patent, please replace the Inventor's address "Burlington, CA (US)" with --Oro-Medonte, Ontario, CA--.

At item (73) on the title page of the patent, please replace the Assignee's address "Burlington, CA" with --Oro-Medonte, Ontario, CA--.

Signed and Sealed this
Twenty-second Day of November, 2016

Michelle K. Lee
*Director of the United States Patent and Trademark Office*